United States Patent [19]

Huge-Jensen et al.

[11] Patent Number: 4,810,414

[45] Date of Patent: Mar. 7, 1989

[54] ENZYMATIC DETERGENT ADDITIVE

[75] Inventors: Ida B. Huge-Jensen, Jae gerspris; Erik Gormsen, Copenhagen, both of Denmark

[73] Assignee: Novo Industri A/S, Bagsvaerd, Denmark

[21] Appl. No.: 91,413

[22] Filed: Aug. 28, 1987

[30] Foreign Application Priority Data

Aug. 29, 1986 [DK] Denmark .............................. 4117/86
Oct. 9, 1986 [DK] Denmark .............................. 4816/86

[51] Int. Cl.$^4$ .......................... C11D 1/00; C11D 7/42; C11D 3/386
[52] U.S. Cl. ...................... 252/174.12; 252/DIG. 12; 435/198; 435/187; 435/188
[58] Field of Search ................... 252/174.12, DIG. 12; 435/198, 187, 188

[56] References Cited

U.S. PATENT DOCUMENTS 4,238,345 12/1980 Guilbert ........................ 252/174.12
4,242,219 12/1980 Bogerman et al. ............. 252/174.12
4,435,307 3/1984 Barbesgaard et al. ......... 252/174.12
4,707,291 11/1987 Thom et al. .................... 252/174.12

Primary Examiner—Paul Lieberman
Assistant Examiner—Ronald A. Krasnow
Attorney, Agent, or Firm—Morris Fidelman; Franklin D. Wolffe

[57] ABSTRACT

Lipase is derived from Humicola sp. (incl. Theremomyces sp.), preferably *H. lanuginosa*. This lipase is found to have high activity at alkaline pH and to be compatible with anionic surfactants, and it is more effective as a detergent additive than previously described detergent lipases.

12 Claims, 2 Drawing Sheets

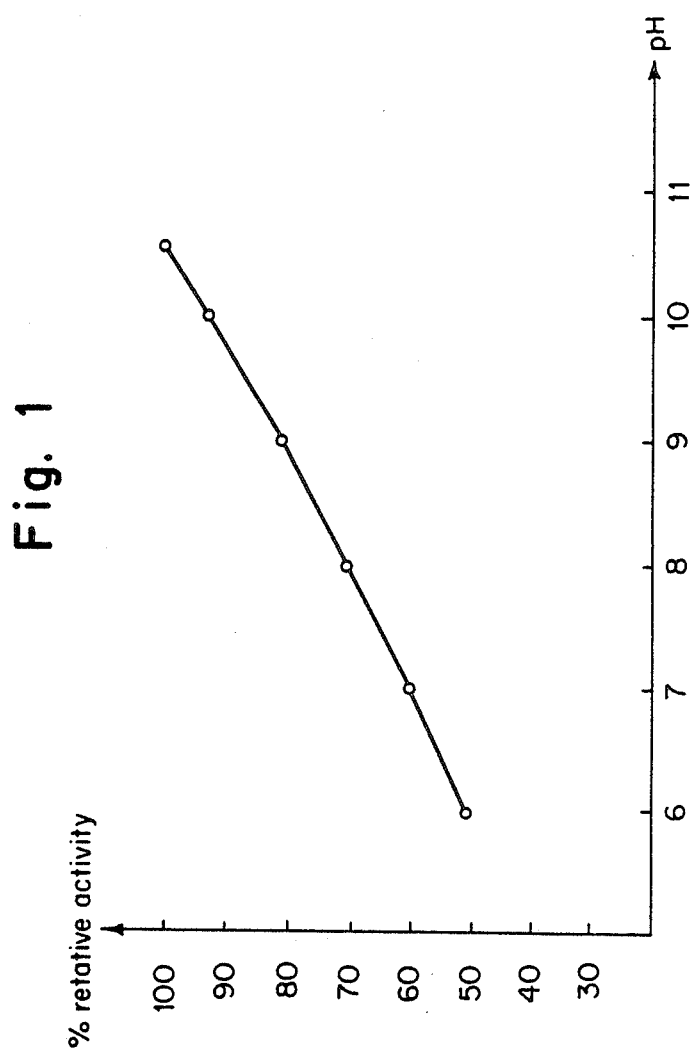

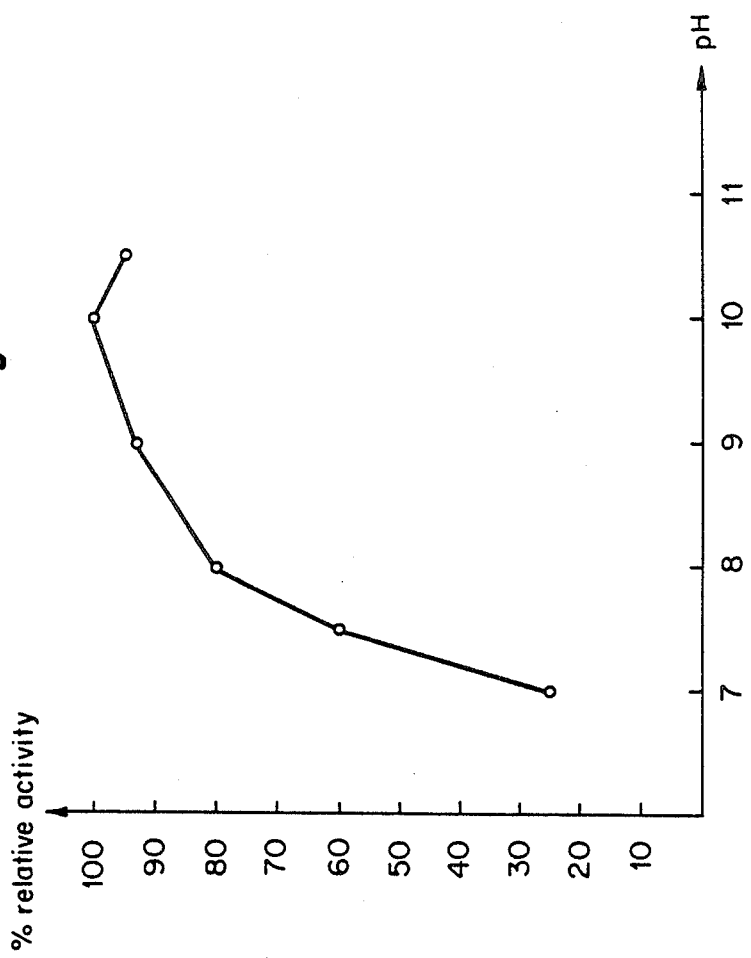

ENZYMATIC DETERGENT ADDITIVE

TECHNICAL FIELD

This invention is related to an enzymatic detergent additive the active component of which is a microbially produced lipase, to a detergent comprising such additive and to a washing process using such detergent.

BACKGROUND OF THE INVENTION

The field comprising enzymatic additives in detergents has been rapidly growing during the last decades. Reference is made to e.g. the article "How Enzymes Got into Detergents", vol. 12, Developments in Industrial Microbiology, a publication of the Society for Industrial Microbiology, American Institute of Biological Sciences, Washington, D.C. 1971, by Claus Dambmann, Poul Holm, Villy Jensen and Mogens Hilmer Nielsen, and to P. N. Christensen, K. Thomsen and S. Branner: "Development of Detergent Enzymes", paper presented on Oct. 9, 1986 at the 2nd World Conference on Detergents held in Montreux, Switzerland.

Proeolytic detergent additive is widely used in Europe, USA and Japan. In several countries, the majority of detergents, both powder and liquid, contain protease.

The use of lipase as a detergent additive is known. For a comprehensive review we refer to H. Andree et al.: "Lipases as Detergent Components", Journal of Applied Biochemistry, 2, 218–229 (1980). Further examples may be found in U.S. Pat. No. 4,011,169 (column 4, line 65 to column 5, line 68), in GB No. 1,293,613 (page 2, lines 6–29) and in the paper by T. Fujii entitled "Washing of Oil Stains with Lipase" (in Japanese) given at the 16. Symposium on Washing, held in Toyko on Sept. 17-18, 1984.

Among the known lipases used as detergent additives, to the best of our knowledge the *Fusarium oxysporum* lipase has the best lipolytic characteristics, looked upon from a detergent application point of view, vide Ser. No. 623,404 filed June 22, 1984, especially the comparative Example 27.

If the washing process is conducted at high temperature and high alkalinity, the majority of the fat containing dirt will be removed anyway. However, low or medium temperature washing processes (around 60° C. and below) are now generally used, and at these low temperatures the known lipases are able to dissolve only a small part of the fat containing dirt.

Hitherto the efficiency of lipolytic detergent additives usually has been measured by washing of EMPA (Eidgenossische Materialprüfungs- und Versuchsanstalt, St. Gallen, Switzerland) swatches Nos. 101 (olive oil/cotton) and 102 (olive oil/wool) by adaptation of the procedure described in British Pat. No. 1,361,386 (especially pages 4 and 7) and U.S. Pat. No. 3,723,250 (especially col. 15-19). In this way lipolytic cleaning efficiency can be expressed as the differential reflectance value ΔR. However, two more direct measures of the lipolytic action have been employed by the inventors hereof. First, the weight of oil remaining on the textile was determined; this shows the combined effect of detergent and lipase. Second, the remaining oil was analyzed for oil (triglyceride) and decomposition products (mono- and diglyceride, and fatty acid), and the number of unhydrolyzed glyceride bonds in the oil was calculated; this shows more directly the effect of lipase. By use of these latter determinations it has been found that even the best known detergent lipase exhibits a lipolytic detergency effect which is open to improvement. The term detergent lipase is intended to refer to lipases having lipolytic action at alkaline pH conditions.

Furthermore, it is common knowledge that lipases, being proteins, are liable to attack by proteases, and as mentioned above, proteases are today contained in many detergents. There is no publication of a detergent lipase having satisfactory stability in the presence of protease. In fact, it has been found that some known detergent lipases have poor stability in detergent solutions in the presence of commonly used detergent proteases.

Thus, a need exists for a lipolytic detergent additive which exhibits a considerably better lipolytic detergent efficiency at economically reasonable lipase activities in the washing solution and which is stable in detergent solutions containing detergent protease.

STATEMENT OF THE INVENTION

The first aspect of the invention provides a lipolytic detergent additive characterized by the fact that the lipase can be produced by cultivation of a strain of the genus Humicola, incl. the genus Thermomyces.

In another aspect, the invention provides a lipolytic detergent additive characterized in that the lipase cross-reacts immunologically with the lipase from *Humicola lanuginosa* strain DSM 3819.

Further aspects of the invention provide a detergent comprising the above-mentioned lipolytic detergent additive and a washing method using this detergent at pH 7–12.

The detergent lipases of the invention shows a superior detergency compared to previously known detergent lipases. Further, the lipases used in the invention are stable in detergent solution in the presence of commonly used detergent proteases, in contrast to many known detergent lipases.

It is described in Japanese unexamined patent publication No. 48-62990 that *Humicola lanuginosa* is a lipase producer. However, this Japanese patent publication fails to suggest that the *H. lanuginosa* lipase is suited as an active component in an enzymatic detergent additive. On the contrary, it appears from FIG. 1 in the Japanese patent publication that the pH-optimum of *H. lanuginosa* lipase is around 8, and that the activity declines sharply when the pH value increases above 8. Thus, it would be expected that this lipase is unsuited as a detergent additive, as the pH in washing solution is usually far above 8. Surprisingly, however, we have found that the *H. lanuginosa* lipase has a pH optimum far above 8, vide Example 1 later in this specification.

Also, it is described in Current Science, August 5, 1981, Vol. 50, No. 15, page 680 that *H. lanuginosa* lipase can be used in dry cleaning. As the pH optimum, which exclusively relates to aqueous media, is of no significance whatsoever in relation to a dry cleaning lipase, this statement is not relevant to a possible suitability of the *H. lanuginosa* lipase as a lipolytic detergent additive.

Furthermore, it appears from Agr.Biol.Chem. 37 (11), p. 2488 (1973) that *H. lanuginosa* lipase is strongly inhibited by addition of certain anionic surfactants. However, we have found that surprisingly *H. lanuginosa* lipase is excellently compatible with LAS, a commonly used anionic surfactant.

DETAILED DESCRIPTION OF THE INVENTION

Lipase-producing microorganisms

Lipases of the invention are preferably obtainable from strains of thermophilic Humicola sp., including thermophilic Thermomyces sp., such as *H. lanuginosa* (Griffon and Maublanc) Bunce, *H. stellata* Bunce, *H. grisea* var. thermoidea, Cooney & Emerson, *H. insolens*, Cooney & Emerson, *Thermomyces ibadanensis*, Apinis & Eggins, *H. hyalothermophila* Moubasher, Mazen and Abdel-Hafez, *H. grisea* var. indica Subrahmanyam, *H. brevis* var. thermoidea Subrahmanyam and Thirumalachar and *H. brevispora* Subrahmanyam and Thirumalachar.

In a specifically preferred embodiment of the enzymatic detergent additive according to the invention the lipase is producible from *H. lanuginosa* (Griffon and Maublanc) Bunce, *H. brevispora* Subrahmanyam and Thirumalachar, *H. brevis* var. thermoidea Subrahmanyam and Thirumalachar or *H. insolens* Cooney & Emerson.

*H. lanuginosa* has also been described under the synonyms *Thermomyces lanuginosus* Tsiklinsky, *Sepedonium lanuginosum* Griffon and Maublanc, *Sepedonium thermaphilum cyclosporum* and *S. thermaphilum ovosporum* Velich, Acremoniella sp. Rege, *Acremoniella thermophila* Curzi and *Monotospora lanuginosa* (Griffon and Maublanc) Mason.

Moreover, the species *Scytalidium thermophilum* (Cooney & Emerson) Austwick was by Hedger (1975, The ecology of thermophilic fungi in Indonesia. In biodegradation et Humification. Rapport due ler Colloque International—Nancy 1974 (ed. G. Kilbertius, O. Reisinger, A. Mourey & J. A. Cancela Da Fonseca), Sarreguemines: Pierron Editeur - 57206) considered as belonging to *Humicola insolens*.

A like uncertainty in assigning an accurate taxonomic designation to many lipase producer species falling within the scope of this invention can be expected. Therefore, for purposes of this invention, Humicola sp. should be construed as including Thermomyces sp. As to preferred embodiments of the invention, the level of uncertainty can be reduced somewhat. Thus, preferred microbial sources of the lipase enzyme are Thermophilic Humicola (including, of course, Thermophilic Thermomyces). For more preferred embodiments of the lipase enzyme, a bio-chemical identification of sorts is possible. The preferred lipase from Humicola sp. strains are those which cross-react immunologically with one or more of the lipases exemplified hereinafter, immunologic identity and partial identity being indicated by the cross-reaction.

In a particular preferred embodiment the lipase is producible from one of the following strains:

| taxonomic designation | internal No. | deposit No. | deposit date |
|---|---|---|---|
| H. lanuginosa | A 1231 | DSM 3819 | 13 Aug 1986 |
| H. lanuginosa | H 126 | DSM 4109 | 4 May 1987 |
| H. brevispora | A 2121 | DSM 4110 | 4 May 1987 |
| H. brevis var. thermoidea | A 2106 | DSM 4111 | 4 May 1987 |
| H. insolens | C 579 | DSM 1800 | 1 Oct 1981 |

DMS indicates Deutsche Sammlung von Mikroorganismen. The strains have been deposited under the terms of the Budapest Treaty.

Lipase for use in the invention may be produced by aerobic cultivation of one of the above strains according to principles known in the art, e.g. as described in the examples given later. It is to be understood that lipases produced by genetic engineering on the basis of Humicola sp. are also within the scope of this invention.

Immunochemical characterization of lipases

The preferred lipases of the invention cross-react immunologically with (are antigenically identical or partially antigenically identical to) a lipase from Humicola sp., more particularly with the lipase from one of the above-mentioned species, particularly *H. lanuginosa* and especially from one of the above-mentioned strains, notably DSM 3819 and DSM 4109.

The identity (cross-reaction) tests can be performed by the well-known Ouchterlony double immunodiffusion procedure or by tandem crossed immunoelectrophoresis according to N.H. Axelsen: Handbook of Immunoprecipitation-in-Gel Techniques (Blackwell Scientific Publication, 1983), Chapters 5 and 14. The terms "antigenic identity" and "partial antigenic identity" are described in the same book, Chapters 5, 19 and 20.

Using monospecific rabbit antiserum raised against purified lipase from DSM 4109, we found that the lipases from strains DSM 3819, DSM 4109, DSM 4110 and DSM 4111 are all antigenically identical by both of the above-mentioned methods. Production of antiserum is described in N. H. Axelsen's book, Chapter 41. Purification of lipase is described in W-H Liu, Agr. Biol. Chem., 37(1), 157–163 (1973); however, we found that the column chromatography may be more conveniently performed by use of: DEAE-sepharose (anion exchange chromatography), phenyl sepharose (hydrophobic interaction chromatography), followed by gel filtration on TSK G3000SW.

Enzymechemical characterization of lipases

The pH dependence of the activity was determined by a traditional method, using trtibutyrin as substrate at 30° C. in a pH stat and with gum arabic as emulsifier. The activity at various pH was found from alkali consumption versus time.

pH dependence was also checked with a more realistic substrate, viz. olive oil adsorbed on PVC (according to U.S. Pat. No. 4,284,719).

pH-activity curves for lipase from *H. lanuginosa* DSM 3819 are shown in FIG. 1 (tributyrin) and FIG. 2 (olive oil/PVC). The curves for DSM 4109, DSM 4110 and DSM 4111 were very similar, showing optimum at pH 10.0–10.5 by both methods. pH-activity curves for lipase from *H. insolens* DSM 1800 are shown in FIG. 3 (tributyrin) and FIG. 4 (olive oil/PVC).

The lipases of this invention are, of course, suited to use at alkaline pH levels; they are good detergent lipases.

Isoelectric focusing was performed on the five lipases, followed by a tributyrin overlayer to detect lipase activity. It was found that DSM 3819, DSM 4109, DSM 4110 and DSM 4111 all have lipase activities with pI around 4.5, while DSM 1800 has the main part of its lipase activity with pI around 9.0–9.5 and only a minute amount of the lipase activity with pI around 4.5.

Detergent additive

In a preferred embodiment, the enzymatic detergent additive according to the invention is provided as a non-dusting granulate or as a liquid. These are suitable for use in powder detergents and liquid detergents, respectively. Granulates can be produced in several different ways. Reference can be made to GB Pat. No. 1,362,365 which describes the production of enzyme containing granulates used as detergent additives by means of an apparatus comprising an extruder and a spheronizer (sold as MARUMERIZER ®), and to U.S. Pat. No. 4,106,991 which describes the production of enzyme containing granulates used as detergent additives by means of a drum granulator.

In the case of a liquid formulation, storage stability tends to be unsatisfactory, and a liquid with an enzyme stabilizer is therefore preferred. The stabilizer can be propylene glycol or other agents known as stabilizers for enzyme solutions. As will be shown later in this specification, a straight aqueous solution of the lipase of the invention has poor storage stability, but this can be remarkably improved by the inclusion of stabilizers, e.g. propylene glycol.

In a specifically preferred embodiment of the enzymatic detergent additive according to the invention, the lipase activity is above about 10,000 LU/g of additive. Lipase Unit (LU) will be defined later in this specification. In this manner, a convenient lipase activity is generated in the washing solution when the detergent additive is added to the detergent in an amount of 0.1 to 5.0 g/100 g of detergent, and when the detergent is added to the washing solution in an amount of 0.5-20 g of detergent/l of washing solution.

In a specifically preferred embodiment, the enzymatic detergent additive according to the invention contains other detergent enzymes besides the lipase, such as protease, amylase or cellulase. Alkaline Bacillus proteases are preferred due to their well-known efficiency as detergent proteases. As such enzymes the proteolytic enzyme ALCALASE ® from NOVO INDUSTRI A/S, manufactured microbially by cultivation of *Bacillus liceniformis,* or the proteolytic enzymes SAVINAWSE ® and ESPERASE ®, also from NOVO INDUSTRI A/S, manufactured according to U.S. Pat. No. 3,723,250, can be used. The mixed enzymatic additive can be prepared either by mixing a previously prepared granulate of proteinase with a previously prepared granulate of lipase, or by mixing a concentrate of proteinase with a concentrate of lipase and then introducing this mixture into a granulating device, together with the usual granulating aids.

Protease is nowadays a common detergent ingredient, and as will be shown later, lipases of the invention are excellently compatible in detergent solution with commercially important detergent proteases, such as those mentioned above. If both lipase and protease are to be added to a detergent it may be convenient to use them in the form of a mixed additive.

In a specially preferred embodiment of the enzymatic detergent additive according to the invention, the proteolytic activity is between about 0.5 and about 3.0 Anson Units/g of additive. In this manner, a convenient proteolytic activity is generated in the washing solution when the detergent additive is added to the detergent in an amount of 0.2-2 g/100 g of detergent, and when the detergent is added to the washing solution in an amount of 0.5-20 g of detergent/l of washing solution. The well-known Anson hemoglobin method for proteolytic activity is described in Journal of General Physiology, 22, 79-89 (1959).

Detergent

In accordance with the previously indicated embodiments of the additive according to the invention, the detergent according to the invention may be a powder or a liquid and may optionally include other detergent enzymes, such as protease, amylase or cellulase, either in the same additive or as separate additives.

In a specially preferred embodiment of the detergent according to the invention, the detergent contains the enzymatic detergent additive according to the invention in an amount of between 0.1 and 5% w/w, more preferably in an amount of 0.2 - 2% w/w. In this manner, a reasonable balance between enzyme action and the action of the other detergent ingredients is generated.

The detergent is typically used in concentrations of 0.5-20 g/l of washing solution, and suitable lipase activity in the washing solution is 1,000-10,000 LU/l, more preferably 1,000-5,000 LU/l. Accordingly, in a preferred embodiment the lipase activity in the detergent is 50-20,000 LU/g, more preferably 50-10,000 LU/g, still more preferably 250-2,000 LU/g and most preferably 500-2,000 LU/g of detergent.

As mentioned above, the preferred lipase in the additive is above 10,000 LU/g, and this is added to the detergents in amounts of preferably 0.1-5% w/w and more preferably 0.2-2% w/w. Accordingly in another preferred embodiment the lipase activity in the detergent is 10-500 LU/g, more preferably 20-200 LU/g of detergent.

In a specially preferred embodiment, the detergent of the invention comprises other detergent enzymes besides the lipase, most preferably a protease. Preferred detergent proteases are those already mentioned. Lipase and protease may be added to the detergent either separately or in the form of a mixed additive. As already mentioned, proteases are commonly used in detergents, and lipases of the invention show a remarkable stability in detergent solution with the commercially important proteases. In accordance with the above-mentioned preferred ranges for protease activity in the additive and for the amount of additive in the detergent, we prefer a protease activity in the detergent of 0.0005-0.15 AU/g, more preferably 0.001-0.060 AU/g, still more preferably 0.003-0.025 AU/g and most preferably 0.006-0.010 AU/g of detergent.

In a specially preferred embodiment of the detergent according to this invention, the surface active material comprises 30-100% anionic and 0-70% non-ionic surfactant, most preferably 50-100% anionic and 0-50% non-ionic surfactant. Detergency of lipase of this invention is specially pronounced in detergents with a high content of anionics, such as LAS (linear alkyl benzene sulfonate).

Washing method

In a specially preferred embodiment of the washing process according to the invention, the washing solution contains the detergent according to the invention in an amount of between 0.5 and 20 g/l of washing solution. In this manner, a convenient lipase activity is generated in the washing solution, i.e. typically between 1,000 and 10,000 LU/l of washing solution, preferably between 1,000 and 5,000 LU/l of washing solution.

BRIEF DESCRIPTION OF THE DRAWINGS

FIGS. 1-4 show pH-activity curves, FIGS. 1-2 are for DSM 3819 lipase, and FIGS. 3-4 for DSM 1800 lipase. FIGS. 1 and 3 are by the tributyrin method, and FIGS. 2 and 4 by the olive oil/PVC method.

EXAMPLES

Lipase activity

The method is based on hydrolysis of tributyrin in a pH-stat. 1 LU (Lipase Unit) is the amount of enzyme which liberates 1 μmol titratable butyric acid per minute at 30° C., pH 7.0 with gum arabic as an emulsifier. Further details are given in Novo analytical Method AF 95/5, available on request.

EXAMPLE 1

Lipase from *H. lanuginosa* DSM 3819

Each of fourty 500 ml shake flasks with 200 ml PL-1C medium (composition indicated below) in each were inoculated with 0.2 ml of a spore suspension prepared on the basis of slants with *H. lanuginosa* DSM 3819 grown on YPG-agar (composition indicated below) for 5 days at 45° C. The thus inoculated shake flasks were shaken 3 days at 45° C. at 240 rpm. At this stage the lipase activity of the accumulated broth (6.7 litres) was 104 LU/ml. The cells were removed by centrifugation at 4000 rpm for 25 minutes. 5.9 liters of supernatant was obtained. The supernatant was filtered through a 10μ nylon filter cloth prior to 8× concentration by ultrafiltration on Pellicon UF Cassette system (membranes with NMWL of 10,000, NMWL being an abbreviation of nominal molecular weight limit).

The UF-concentrate (final volume of 740 ml) was converted to a crude powder by freeze-drying. This crude powder exhibited a lipase activity of 13,310 LU/g.

| Composition of YPG-agar was as follows: | |
|---|---|
| Yeast extract, Difco | 4 g/l |
| Glucose | 15 g/l |
| $K_2HPO_4$ | 1 g/l |
| $MgSO_4, 7H_2O$ | 0.5 g/l |
| Agar | 20 g/l |
| Autoclaved at 121° C. for 40 minutes. | |
| Composition of PL-1c medium was as follows: | |
| Peptone | 15 g/l |
| Tween-80 | 18 g/l |
| $MgSO_4, 7H_2O$ | 2 g/l |
| $CaCl_2, 2H_2O$ | 0.1 g/l |
| Nalco-10 | 2 g/l |
| pH before autoclaving | 6.0 |
| Autoclaved at 121° C. for 40 minutes. | |

EXAMPLE 2

Lipase from other Humicola strains

Strain DSM 4111 was fermented on medium PL-1c, strain DSM 4109 on medium GT, strain DSM 4110 on medium GTS-1, and strain DSM 1800 on medium LR-8ST, essentially as described in Example 1.

| Composition of fermentation media: | | | | |
|---|---|---|---|---|
| | | GT | GTS-1 | LR-8ST |
| Yeast extract (65% dry matter) | g/l | 22.5 | 15 | 0 |
| Pharmamedia | — | 0 | 0 | 50 |
| Tween 80 | — | 18 | 5 | 5 |
| Span 80 | — | 0 | 5 | 5 |
| $MgSO_4, 7H_2O$ | — | 2 | 2 | 0.5 |
| $CaCl_2, 2H_2O$ | — | 0.1 | 0.1 | 0 |
| $K_2HPO_4$ | — | 0 | 0 | 5 |
| $NaNO_3$ | — | 0 | 0 | 1 |
| Nalco-10 | — | 5 | 2 | 0 |
| pH before autoclaving | — | ~6.5 | ~6.0 | ~7.0 |

Recovery from the culture broths was performed essentially as described for DSM 3819 in Example 1. In the instance of lipase from DSM 4109, an additional purification step was performed prior to freeze-drying: the UF-Concentrate was precipitated with acetone whereafter the precipitate was redissolved in water and freeze-dried. The resulting freeze-dried powders exhibited the following lipase activities:

| Strain | DSM 4111 | DSM 4109 | DSM 4110 | DSM 1800 |
|---|---|---|---|---|
| LU/g | 32,000 | 211,000 | 6,600 | 1,800 |

Washing method

The test material employed for washing trials was cotton fabric (with a surface weight corresponding to around 1.2 g/50 cm$^2$) impregnated with olive oil (Sigma 0–1500). The swatches were produced simply by dropping 50 or 85 μl (as indicated) of olive oil heated to 50°–60° C. on the centre of each test swatch (7×7 cm) by means of a micropipette. After oil application, the swatches were aged at room temperature for about 2 days.

The lipase preparations from Examples 1 and 2 were used in the washing examples given hereafter, each identified by the strain number.

Also, for comparison, a lipolytic powder on the basis of *Fusarium oxysporum*, obtained as described in Example 23 in Ser. No. 623,404 filed June 22, 1984, and representing the most efficient previously known lipolytic detergent additive, was used. The activity of the *Fusarium oxysporum* lipase preparation was 90,000 LU/g.

The lipases were evaluated in washing tests in a Terg-O-Tometer test washing machine. The Terg-O-Tometer test washing machine is described in Jay C. Harris, Detergency evaluation and testing, Interscience Publishers Ltd., 1954, pages 60–61.

The washing trials were carried out under the following condition:
Agitation: 100 rpm
Water hardness: 18° German hardness (tap water) unless otherwise noted
Cloth/liquid ratio: 7 swatches/1000 ml
Rinsing: 15 min in running tap water
The amount of oil contained in 7 swatches with 85 μl each is approx. 535 mg (density 0.90).

After rinsing, the swatches were air dried. The residual oil content in the swatches was determined by Soxhlet extraction with n-hexane for 5 hours followed by gravimetric determination of residual matter.

The composition of the residual oil was analyzed by the TLC-FID (TLC/FID is an abbreviation for thin layer chromatography/flame ionization detector, the method being described in Lipids, vol. 18, No. 10 (1983), page 732) method using a Iatroscan TH-10 (Iatron Lab. Inc., Tokyo) combined with a Chromatocorder II (System Instruments Co., Ltd., Tokyo) computing integrator under the following conditions:
Stationary phase: Chromarod S-II (Iatron)
Mobile phase: Hexane/chloroform/acetic acid (60:50:2 v/v/v)
Hydrogen flow rate: 160 ml/min
Air flow rate: 2000 ml/min
Scan speed: 30 sec per scan
Samples for the TLC-FID analysis were prepared as follows. After gravimetrical determination of residual matter the dried extract was redissolved in 20 ml of hexane and 5 ml of an internal standard (lithocholic acid, 12.5 mg/ml) dissolved in ethanol was added. 1 μl of sample was used for each analysis.

Based on standard curves for triolein, diolein, monoolein, and oleic acid the relative composition (% w/w) of the residual oil was calculated.

The number of unhydrolyzed glyceride bonds in the residual oil was calculated using the following formula:

$$n = 10 \times M\left(\frac{3}{885} \times X_{TG} + \frac{2}{621} \times X_{DG} + \frac{1}{357} \times X_{MG}\right)(\mu \text{ mole})$$

where
$X_{TG}$ is the percentage of triglyceride (% w/w)
$X_{DG}$ is the percentage diglyceride (% w/w)
$X_{MG}$ is the percentage monoglyceride (% w/w)
M is the residual amount of oil (mg) 885, 621, and 357 are the mole weights for triolein, diolein, and monoolein, respectively.

EXAMPLE 3

Effect of washing temperature

This example demonstrates the effect of the Humicola lanuginosa lipase (DSM 3819) in an anionic detergent at different wash temperatures.

Detergent composition: LAS (0.5 g/l), Na$_2$CO$_3$ (1.0 g/l)
Washing time: 20 min.
Lipase dosage: 3000 LU/l
pH: 9.5
Soiling: 85 μl olive oil
LAS is a linear alkyl benzene sulfonate (Nansa HS80/S, Albright & Wilson), an anionic surfactant.

| Temp. | | Without lipase | *Fusarium oxysporum* | *Humicola lanuginosa* |
|---|---|---|---|---|
| 30° C. | Residual oil (mg) | 185 | 187 | 165 |
| | n (μmole) | 590 | 571 | 360 |
| 50° C. | Residual oil (mg) | 187 | 192 | 157 |
| | n (μmole) | 606 | 628 | 432 |

EXAMPLE 4

Effect of washing time

In this example the effect of the Humicola lanuginosa lipase (DSM 3819) is demonstrated using different washing times.

Detergent composition: LAS (0.5 g/l), Na$_2$CO$_3$(1.0 g/l)
Temperature: 30° C.
Lipase dosage: 3000 LU/l
pH (initial): 9.5
Soiling: 85 μl olive oil

| Washing time (min.) | | Without lipase | *Fusarium oxysporum* | *Humicola lanuginosa* |
|---|---|---|---|---|
| 20 | Residual oil (mg) | 185 | 187 | 165 |
| | n (μmole) | 590 | 571 | 360 |
| 40 | Residual oil (mg) | 177 | 167 | 128 |
| | n (μmole) | 568 | 526 | 246 |
| 60 | Residual oil (mg) | 141 | 147 | 93 |
| | n (μmole) | 465 | 454 | 153 |
| 90 | Residual oil (mg) | 139 | 135 | 78 |
| | n (μmole) | 431 | 419 | 111 |

EXAMPLE 5

Effect of washing hardness on washing

This example shows the influence of water hardness on the detergency of Humicola lanuginosa lipase (DSM 3819). The hardness (°GH=°German hardness) was adjusted by mixing tap water and distilled water.

Detergent composition: LAS (0.5 g/l), Na$_2$CO$_3$ (1.0 g/l)
Temperature: 30° C.
Washing time: 20 min.
Lipase dosage: 3000 LU/l
pH (initial): 9.5
Soiling: 85 μl olive oil

| Hardness °GH | | Without lipase | *Fusarium oxysporum* | *Humicola lanuginosa* |
|---|---|---|---|---|
| 0 | Residual oil (mg) | 254 | 244 | 242 |
| | n (μmole) | 820 | 752 | 627 |
| 6 | Residual oil (mg) | 210 | 192 | 173 |
| | n (μmole) | 670 | 595 | 415 |
| 12 | Residual oil (mg) | 182 | 179 | 170 |
| | n (μmole) | 579 | 548 | 405 |
| 18 | Residual oil (mg) | 185 | 187 | 165 |
| | n (μmole) | 590 | 571 | 360 |

EXAMPLE 6

Effect of lipase dosage on washing

This example shows the influence of dosage of H. lanuginosa lipase on washing performance, using acetone fractionated lipase powder from DSM 3819.

Acetone fractionation was done on 10g of the crude powder prepared in Example 1, dissolved in water to 104 ml total volume. Final acetone concentration was 45% by volume. After freeze-drying the re-dissolved acetone precipitate, 0.629 g with an activity of 160,960 LU/g was obtained. This was used in the following washing tests.

Detergent composition: LAS (0.5 g/l), Na$_2$CO$_3$ (1.0 g/l)
Washing time: 20 min
Temperature: 30° C.
pH (initial): 9.5
Soiling: 85 μl olive oil
The soiled swatches used were a different batch from Examples 2–5, so results are not directly comparable.

| Lipase dosage, LU/ml | 0 | 500 | 1500 | 3000 | 6000 | 10,000 |
|---|---|---|---|---|---|---|
| Residual oil (mg) | 232 | 209 | 202 | 202 | 194 | 176 |
| n (μmole) | 761 | 558 | 521 | 471 | 437 | 363 |

EXAMPLE 7

Comparison of Humicola lipases in washing

This example compares the washing effect obtained with lipase from *H. lanuginosa* (DSM 4109), *H. brevis* var. *thermoidea* (DSM 4111), *H. brevispora* (DSM 4110) and *H. insolens* (DSM 1800).

| Detergent composition: | LAS | 0.50 g/l |
| --- | --- | --- |
| | Tallow soap | 0.05 — |
| | Alcoholethoxylate (C$_{12-14}$,6EO) | 0.10 — |
| | Alcoholethoxylate (C$_{16-18}$,30EO) | 0.02 — |
| | Zeolite | 1.20 — |
| | Na$_2$CO$_3$ | 0.50 — |
| | Sodium metasilicate | 0.10 — |
| | EDTA (titriplex III) | 0.01 — |
| | Na$_2$SO$_4$ | 2.00 — |
| Temperature: | 30° C. | |
| Washing time: | 20 min | |
| Lipase dosage: | 6000 LU/l | |
| pH: | 9.5 | |
| Soiling: | 50 μl (olive oil) | |
| Lipase preparation | n (μmoles) | |
| none | 546 | |
| H. lanuginosa | 454 | |
| H. brevis var. thermoidea | 468 | |
| H. brevispora | 484 | |
| H. insolens | 350 | |

EXAMPLES 8

Protease stability of Humicola lipases

The excellent stability of Humicola lipases in detergent solutions containing proteolytic enzymes is demonstrated below.

A *Humicola lanuginosa* preparation (DSM 4109) is compared to the Fusarium oxysporum lipase used in previous examples and to the commercial lipase preparation, Amano P (Amano Pharmaceutical co. Ltd., Nagoya, Japan), which is produced by *Pseudomonas fluorescens*.

The alkaline Bacillus proteases ALCALASE, SAVINASE and ESPERASE were used. These are commercial detergent proteases from Novo Industri A/S, Denmark.

The proteolytic activity was determined with casein as the substrate. One Casein Protease Unit (CPU) is defined as the amount of enzyme liberating 1 mM of primary amino groups (determined by comparison with a serine standard) per minute under standard conditions, i.e. incubation for 30 mintues at 25° C. and pH 9.5. A 2% (w/v) solution of casein (Hammersten, supplied by Merck A.G., West Germany) was prepared with the Universal Buffer described by Britton and Robinson (Journ. Chem. Soc. 1931, p. 1451) adjusted to pH 9.5.

Detergent: 1.3 g/l of a non-phosphate powder containing 25% surfactant (alphaolefin sulphonate (AOS) and linear alkyl-benzene sulphonate (LAS)), sodium sulphate, zeolite, sodium silicate and optical brightener.

Water hardness: 4.5° German hardness
pH: 10.0 (adjusted)
Temperature: 25° C.
Lipase activity (initial): 3000 LU/l
Protease activity: 0 or 0.05 CPU/l
Residual lipase activity (%):
(1) Protease: SAVINASE

| | Incubation time (min) | | | | |
| --- | --- | --- | --- | --- | --- |
| Lipase | 0 | 15 | 30 | 60 | 90 |
| Humicola lanuginosa | 100 | 99 | 94 | 91 | 89 |
| Fusarium oxysporum | 100 | 32 | 14 | 3 | — |
| Pseudomonas fluorescens | 100 | 1 | 0 | — | — |

(2) Protease: None

| | Incubation time (min) | | | | |
| --- | --- | --- | --- | --- | --- |
| Lipase | 0 | 15 | 30 | 60 | 90 |
| Humicola lanuginosa | 100 | 101 | 99 | 102 | 96 |
| Fusarium oxysporum | 100 | 57 | 42 | 18 | 6 |
| Pseudomonas fluorescens | 100 | 94 | 94 | 88 | 90 |

Detergent:
LAS: 0.40 g/l
Alcoholethoxylate (Berol 065): 0.15 g/l
Tallow soap: 0.15 g/l
Sodium tripolyphosphate: 1.50 g/l
Sodium metasilicate: 0.40 g/l
CMC: 0.05 g/l
Na$_2$SO$_4$: 2,10 g/l
Water hardness: 18° German hardness
pH: 9.5
Temperature: 30° C.
Lipase activity: 3000 LU/l
Protease activity: 0 or 0.05 CPU/l
(1) Protease: SAVINASE

| | Incubation time (min) | | | | |
| --- | --- | --- | --- | --- | --- |
| Lipase | 0 | 15 | 30 | 60 | 90 |
| Humicola lanuginosa | 100 | 99 | 98 | 97 | 97 |
| Fusarium oxysporum | 100 | 5 | 0 | — | — |
| Pseudomonas fluorescens | 100 | 0 | — | — | — |

(2) Protease: ALCALASE

| | Incubation time (min) | | | | |
| --- | --- | --- | --- | --- | --- |
| Lipase | 0 | 15 | 30 | 60 | 90 |
| Humicola lanuginosa | 100 | 98 | 97 | 95 | 95 |
| Fusarium oxysporum | 100 | 24 | 4 | 0 | — |
| Pseudomonas fluorescens | 100 | 18 | 0 | — | — |

(3) Protease: ESPERASE

| | Incubation time (min) | | | | |
| --- | --- | --- | --- | --- | --- |
| Lipase | 0 | 15 | 30 | 60 | 90 |
| Humicola lanuginosa | 100 | 97 | 96 | 96 | 98 |
| Fusarium oxysporum | 100 | 20 | 0 | — | — |
| Pseudomonas fluorescens | 100 | 0 | — | — | — |

(4) Protease: None

| | Incubation time (min) | | | | |
| --- | --- | --- | --- | --- | --- |
| Lipase | 0 | 15 | 30 | 60 | 90 |
| Humicola lanuginosa | 100 | 96 | 95 | 96 | 94 |
| Fusarium oxysporum | 100 | 30 | 10 | 0 | — |
| Pseudomonas fluorescens | 100 | 101 | 102 | 102 | 99 |

It is seen that the Humicola lipase of the invention is very stable in detergent solution with protease, in contrast to prior-art detergent lipases (fusarium and Pseudomonas).

EXAMPLE 9

Stabilized liquid Humicola lipase preparations

Lipase stability in solutions with various stabilizers was investigated.
Lipase: Humicola lanuginosa (DSM 4109)
Storage temp: 30° C.
pH: 7.0

Rodalon ™ was added to all preparations as a preservative (0.2 mg active matter per ml).

Results:

| 1,2-propanediol (ml/ml) | Sorbitol (g/ml) | CaCl$_2$.2H$_2$O (mg/ml) | INITITAL ACTIVITY (LU/ml) | Residual activity (%), days | | | | |
|---|---|---|---|---|---|---|---|---|
| | | | | 0 | 2 | 13 | 29 | 49 |
| 1 | 0 | 0 | 0 | 4520 | 100 | 17 | 2 | <1 | <1 |
| 2 | 0.50 | 0 | 0 | 4520 | 100 | 93 | 63 | 35 | 34 |
| 3 | 0.50 | 0 | 3 | 4720 | 100 | 86 | 76 | 54 | 48 |
| 4 | 0 | 0.30 | 0 | 4880 | 100 | 57 | 10 | <1 | <1 |

These results demonstrate that 1,2-propanediol (MPG=mono propylene glycol) is an excellent stabilizer for Humicola lipase. The storage stability may be further improved by adding Ca salt. Sorbitol has a slight stabilizing effect.

A wash trial was carried out with a stabilized liquid lipase preparation with the following composition:
Humicola lanuginosa DSM 4109 lipase: 5000 LU/ml
1,2-propanediol: 50% v/v
Deionized water: 50% v/v
CaCl$_2$.2H$_2$O: 3 mg/ml
Detergent composition: LAS (0.5 g/l), Na$_2$CO$_3$ (1.0 g/l)
Temperature: 30° C.
Washing time: 20 minutes
pH: 9.5
Soiling: 50 μl olive oil
Lipase dosage: 1 ml stabilized liquid preparation per liter wash liquor.

Results:

| Lipase dosage LU/l | Residual oil (mg) | n (μmoles) |
|---|---|---|
| 0 | 157 | 507 |
| 5000 | 145 | 418 |

EXAMPLE 10

Humicola lipase as dust-free granulate

A carrier granulate without enzyme was prepared essentially according to U.S. Pat. No. 4,106,991 with the following composition:
15% cellulose fibres
4% titanium dioxide
5% yellow dextrin
10% sucrose
64% sodium sulphate This granulate was sieved to obtain a 300-710 μm particle size.

30.8 g of this was wetted by 6.2 g of a 30% solution in ethanol of polyvinylpyrrolidon (PVP K30, product of GAF Corp., USA). After thorough mixing, 12.3 of freeze-dried *H. lanuginosa* DSM 4109 lipase (92,700 LU/g, prepared essentially as in Example 2) was added, and was thoroughly mixed. The granulate was dried (evaporation of ethanol) by air blowing (fluidization) at about 50° C. 300-850 μm particles were collected by sieving.

The granulate was then coated in three steps, as follows:
5% of polyethyleneglycol (MW 600)
11.25% of TiO$_2$/Mg silicate (4:1)
4% of polyethyleneglycol (MW 600)

The coated granulate was air-blown at 0.8 m/sec for 10 minutes to remove fine particles of coating material.

Finally, the material was sieved again, and the 300-850 μm range was collected. A dust-free, off-white granulate was obtained.

Yield and activity were as follows:

| freeze-dried powder | 92,700 LU/g | 12.3 g |
| un-coated granulate | 21,100 — | 45.0 — |
| coated granulate | 18,200 — | |

A washing trial was carried out with the freeze-dried powder and the granulate as follows:
Detergent composition: LAS (0.5 g/l), Na$_2$CO$_3$ (1.0 g/l)
Temperature: 30° C.
Washing time: 20 minutes
Lipase dosage: 6000 LU/l
pH: 10.0
Soiling: 50 μl olive oil Results:

| Lipase preparation | n (μmoles) |
|---|---|
| none | 515 |
| freeze-dried powder | 386 |
| granulate | 415 |

We claim:

1. A lipolytic and proteolytic enzymatic detergent additive in the form of a non-dusting granulate or a stabilized liquid,
   the active lipolytic enzyme component of which is a lipase produced by lipase producing strain of a Humicola sp., said lipase being characterized by high activity at alkaline pH, stability in protease containing detergent solutions and compatibility with anionic surfactants, the lipase activity of said additive being above 10,000 LU/g of additive, and,
   the proteolytic enzyme component of which is an alkaline Bacillus protease the protease activity being between about 0.5 and 3.0 Anson units per gram of additive.

2. An enzymatic detergent additive according to claim 1 wherein the lipase producing strain of Humicola is a strain belonging to *H. lanuginosa* (Griffon and Maublanc) Bunce, *H. brevispora* Subrahmanyam and Thirumalachar, *H. brevis* var. thermoidea Subrahmanyam and Thiramulacher or *H. insolens* Cooney & Emerson.

3. Enzymatic detergent additive according to claim 2, wherein the strain is *H. lanuginosa* DSM 3819.

4. An enzymatic detergent additive in the form of a non-dusting granulate or a liquid according to claim 2, the active lipolytic component of which is a microbially produced lipase, wherein the lipase cross-reacts immunologically with the lipase from *Humicola lanuginosa* strain DSM 3819.

5. Enzymatic detergent additive according to claim 1, wherein the additive is a liquid, the liquid containing therein an enzyme stabilizer.

6. Enzymatic detergent additive according to claim 5, wherein the stabilizer is propylene glycol.

7. Detergent according to claim 8, wherein the detergent composition includes therein a surface active material comprising from 30 to 100 weight % of anionic surfactant and up to 70 weight % of non-ionic surfactant.

8. A detergent composition having incorporated therein effective levels of lipase and protease in non-dusting granulate additive form or in stabilized liquid additive form wherein the lipase activity exceeds 10,000 LU/g of lipase additive and wherein the protease activity is 0.5-3 Au/g of protease additive, the lipase being a lipase producible by a strain of Humicola sp. said lipase being characterized by high activity at alkaline pH, stability in the presence of protease, and compatibility with anionic surfactants, and the protease being an alkaline Bacillus protease.

9. A detergent composition as in claim 8 further comprising a mixed enzyme additive incorporated therein.

10. A detergent composition as in claim 8 further comprising lipase and protease in additive form as from 0.1–5.0% by weight of the detergent composition.

11. A detergent composition as in claim 8 further comprising a lipase content therein adapted to provide lipase activity in wash water to which the detergent composition is added of 1000–10,000 LU per liter.

12. A washing process which comprises washing at a temperature below about 60° C. at a pH between 7 and 12 with from 0.5–20 g/l of a detergent composition the wash water having incorporated therein;

a lipolytic enzyme additive with a lipase activity above 10,000 LU/g of additive, the enzyme component of which is a lipase produced by a lipase producing strain of a Humicola sp., said lipase being characterized by high activity at alkaline pH, stability in the presence of protease and compatibility with anionic surfactants, the lipase concentration in the wash water being from 1000–10,000 LU/l; and a proteolytic additive with a protease activity of 0.5–3 AU/g of additive in effective amount, the enzyme of which is a alkaline Bacillus protease.

* * * * *